(12) United States Patent
Alhourani

(10) Patent No.: US 9,962,503 B2
(45) Date of Patent: May 8, 2018

(54) SPRING HYPODERMIC NEEDLE

(71) Applicant: Rakan Alhourani, Alfuhais (JO)

(72) Inventor: Rakan Alhourani, Alfuhais (JO)

(*) Notice: Subject to any disclaimer, the term of this patent is extended or adjusted under 35 U.S.C. 154(b) by 106 days.

(21) Appl. No.: 14/998,023

(22) Filed: May 20, 2015

(65) Prior Publication Data
US 2017/0043104 A1  Feb. 16, 2017

(51) Int. Cl.
*A61M 5/46*  (2006.01)
*A61B 17/34*  (2006.01)

(52) U.S. Cl.
CPC .......... *A61M 5/46* (2013.01); *A61B 17/3403* (2013.01)

(58) Field of Classification Search
CPC ..... A61M 5/46; A61M 5/329; A61B 17/3403; A61B 2017/3409
USPC .................................................... 604/168.01
See application file for complete search history.

(56) References Cited

U.S. PATENT DOCUMENTS

| | | | | |
|---|---|---|---|---|
| 5,139,485 A * | 8/1992 | Smith | A61B 17/3496 | 604/158 |
| 5,312,351 A * | 5/1994 | Gerrone | A61B 17/3417 | 604/117 |
| 5,334,159 A * | 8/1994 | Turkel | A61B 17/3496 | 604/158 |
| 6,638,251 B2 * | 10/2003 | Steube | A61B 17/3415 | 604/158 |
| 8,608,697 B2 * | 12/2013 | Tran | A61M 13/00 | 604/117 |
| D735,847 S * | 8/2015 | Laurence | D24/112 | |
| 9,616,203 B2 * | 4/2017 | Donaldson | A61M 27/00 | |
| 2002/0188254 A1 * | 12/2002 | Steube | A61B 17/12045 | 604/101.03 |
| 2003/0120297 A1 * | 6/2003 | Beyerlein | A61B 17/3478 | 606/185 |
| 2007/0179455 A1 * | 8/2007 | Geliebter | A61M 5/329 | 604/272 |
| 2009/0048622 A1 * | 2/2009 | Wilson | A61B 17/3431 | 606/190 |
| 2010/0094216 A1 * | 4/2010 | Yue | A61M 5/46 | 604/117 |
| 2010/0210934 A1 * | 8/2010 | Belson | A61M 25/0105 | 600/371 |
| 2012/0108926 A1 * | 5/2012 | Kassab | A61B 17/3403 | 600/323 |
| 2016/0074146 A1 * | 3/2016 | Goddard | A61F 2/0045 | 606/151 |
| 2016/0135842 A1 * | 5/2016 | Kassab | A61B 17/3496 | 600/345 |
| 2017/0043104 A1 * | 2/2017 | Alhourani | A61M 5/46 | |

* cited by examiner

*Primary Examiner* — Matthew F Desanto

(57) ABSTRACT

A needle that consists of two pieces: the first piece has a tip, a shaft, a spring and a bi-color indicator, and the second piece has two parallel hollow lumens; one lumen is for fluid entrance and passage, and the other lumen configured to receive the first piece. When the hypodermic needle tip touches the skin or being inside a tissue the spring will be squeezed and the first piece will be situated backward in its primary position. When the tip of the needle just enters any cavity or any vessel the spring will be freed and pushes the first piece forward with the change of the color of the bicolored indicator.

1 Claim, 7 Drawing Sheets

SPRING HYPODERMIC NEEDLE

CROSS-REFERENCES TO RELATED APPLICATIONS

Not Applicable

STATEMENT REGARDING FEDERALLY SPONSORED RESEARCH OR DEVELOPMENT

Not Applicable

STATEMENT REGARDING PRIOR DISCLOSURES BY THE INVENTOR OR A JOINT INVENTOR

Not Applicable

FIELD OF THE INVENTION

The present invention relates to a needle and a cannula that allow us to know immediately when the tip of the needle or the cannula just gets inside a cavity or a blood vessel.

BACKGROUND OF THE INVENTION

When using an ordinary needle to get a blood sample from or to inject medication in a blood vessel, we enter blindly through the skin and tissue to reach the vessel, so it is possible to get in and continue out of the vessel without even knowing that we pass through it, which unfortunately will rupture the vessel and cause discomfort to the patient, so one application of the spring hypodermic needle is that it prevents the blindly passing through a vessel. Another application is with many emergency cases when we have a collapsed patient who needs immediate cannula insertion, and in those cases the blood vessels are collapsed and attenuated, which makes it difficult to get in, so the usage of the spring hypodermic needle and cannula will make it easier and quicker to get inside a vessel and save patient's life. Another application is in lumber puncture procedure, as it is known we enter blindly using regular needles that may eventually induce injuries and serious complications to the spine, and by using the spring hypodermic needle we will know immediately when the needle just gets inside the spinal cavity, so we avoid and prevent serious complications.

SUMMARY OF THE INVENTION

The present invention is a needle with detecting piece that moves forward by the force of a spring, when the tip of the needle just enters a lumen, a blood vessel or a cavity.

DETAILED DESCRIPTION OF THE INVENTION

Figure 1:
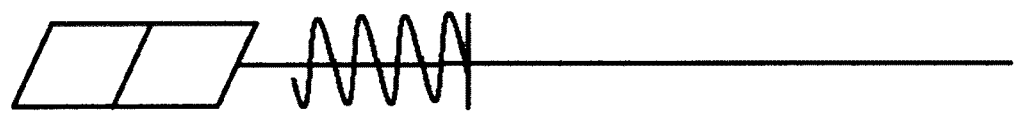
FIG. 1: The first piece.
Figure 2:
FIG. 2: The tip of the first piece.
Figure 3:
FIG. 3: The shaft of the first piece.
Figure 4:
FIG. 4: The spiral spring part of the first piece.
Figure 5:
FIG. 5: The bi-color indicator part of the first piece (red/green).
Figure 6:
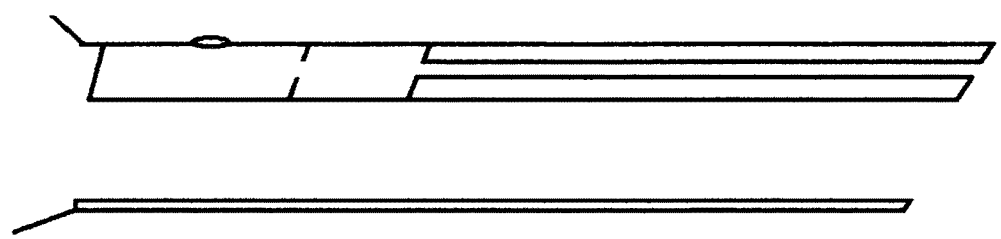
FIG. 6: The second piece.
Figure 7:
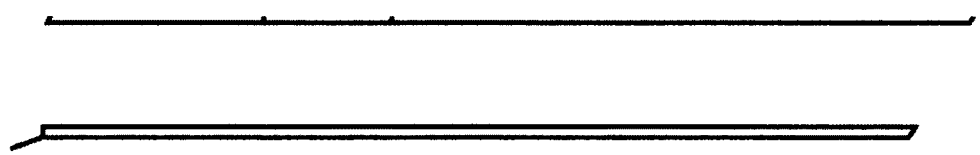
FIG. 7: The fluid passage part of the second piece.
Figure 8:
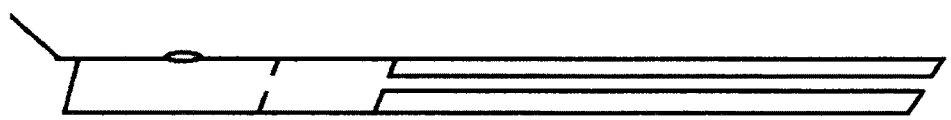
FIG. 8: The container part of the second piece (it contains and is configured to receive the first part).
Figure 9:
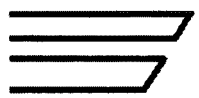
FIG. 9: The tip of the container part of the second piece—the needle tip—.
Figure 10:
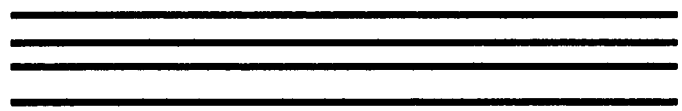
FIG. 10: The shaft of the container part of the second piece.
Figure 11:
FIG. 11: The spiral spring container part of the container part of the second piece (it contains the spiral spring part of the first piece).
Figure 12:
FIG. 12: The indicator container part of the container part of the second piece (it has a hole that shows the color of the bi-color indicator part of the first piece inside).
Figure 13:
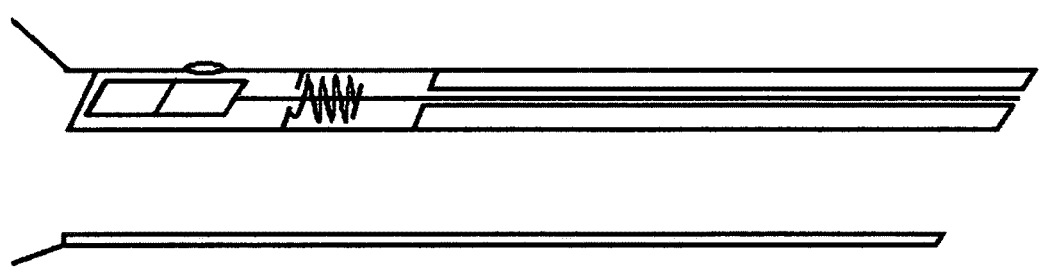
FIG. 13: This drawing illustrates the two pieces together when the needle's tip is inside a tissue.
Figure 14:
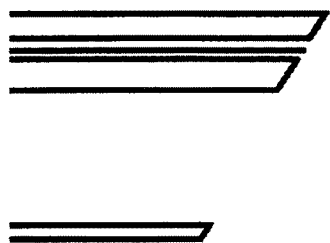
FIG. 14: The tip of the first piece is inside the needle's tip (the second piece).
Figure 15:
FIG. 15: The spring is squeezed and the indicator shows the green color.
Figure 16:
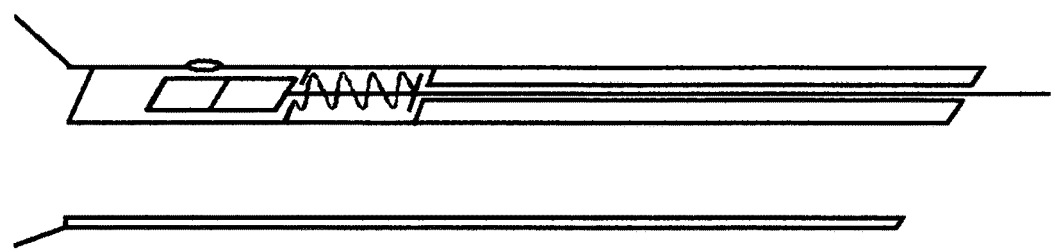
FIG. 16: This drawing illustrates the two pieces together when the needle's tip just enters a cavity or a vessel.
Figure 17:
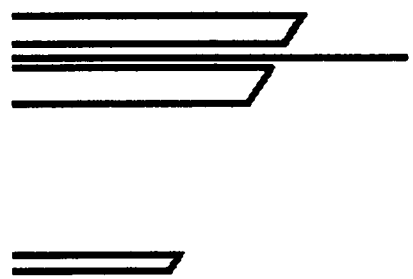
FIG. 17: The first piece's tip is moved forward beyond the level of the second piece's tip.
Figure 18:
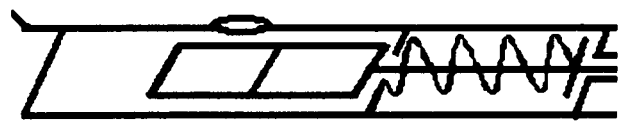
FIG. 18: The spring is freed and the indicator shows the red color.

The spring hypodermic needle comprising two pieces: the first piece FIG. 1 has four parts; bi-color indicator part (green and red) FIG. 5, spiral spring part FIG. 4, shaft part FIG. 3 and tip part FIG. 2. The second piece FIG. 6 has two hollow lumens; a lumen for fluid entrance and passage (the fluid passage part of the second piece) FIG. 7, and a lumen that is configured to receive the first piece (the container part of the second piece) FIG. 8; the container part of the second piece consists of four parts: The tip FIG. 9 that is configured to receive the tip of the first piece, the shaft FIG. 10 that is configured to receive the shaft of the first piece, the spiral spring container part FIG. 11 that is configured to receive the spiral spring part of the first piece, and the indicator container part FIG. 12 that is configured to receive the bi-color indicator part of the first piece (the indicator container part FIG. 12 has a hole through which the color inside appears). When the needle's tip is inside a body tissue FIG. 13, the first piece's tip will find resistance to move forward in relation to the second piece, so the tip of the first piece is at the level of the bevel or the tip of the needle FIG. 14 (it is not moved forward beyond the level of the needle's tip), in this position the green color is showing through the hole of the second piece's indicator container part, and the spring of the first piece is squeezed FIG. 15 and just stands by in this position till the tip of the first piece is freed, and that happens when the tip of the needle enters a cavity or a lumen or a blood vessel. When the needle's tip is just entering any cavity or blood vessel FIG. 16, there will be no more resistance against the first piece's tip movement and accordingly no more resistance against the spring, so the spring will be freed FIG. 18 and displaces the whole first piece forward including the tip, shaft and the bi-color indicator part, so the tip of the first piece will be displaced forward FIG. 17; the first piece's tip level will move forward beyond the needle's bevel level and the color that is showing through the hole of the second piece's indicator container part will change from green to red. This invention is also applicable to the needle of a cannula.

What is claimed is:
1. A needle device comprising two pieces,
   a first piece comprising bi-color indicator part having a first color and second different color, spring part, shaft part and tip part, and a second piece comprising a needle with two parallel hollow lumens and a tip, said needle comprising a first lumen with a fluid passage part configured for fluid entrance, and a second lumen with a container part configured to receive the first piece; the container part of the second piece comprising a tip portion configured to receive the first piece tip part, a shaft configured to receive the first piece shaft part, a spring container configured to receive the first piece spring part, and an indicator container configured to receive the first piece bi-color indicator part, the indicator container has a hole through which the color of the bi-color indicator part appears;

wherein the needle device has a primary position in which the spring part of the first piece is not compressed, the first color of the bi-color indicator is displayed through the hole of the indicator container and the whole structure of the first piece is displaced forward in relation to the second piece; a secondary position in which the spring part of the first piece is compressed, the tip of the first piece is coplanar with the tip of the needle and the second color of the bi-color indicator is displayed through the hole of the indicator container, and the needle device is configured to change the color of the bi-indicator color part based on pressure and resistance against the tip of the first piece and compression of the spring part of the first piece.

\* \* \* \* \*